US006879154B2

(12) United States Patent
Fleury

(10) Patent No.: US 6,879,154 B2
(45) Date of Patent: Apr. 12, 2005

(54) METHOD FOR DETERMINING THE RESISTIVITY INDEX, AS A FUNCTION OF THE WATER SATURATION, OF CERTAIN ROCKS OF COMPLEX POROSITY

(75) Inventor: Marc Fleury, La Celle Saint Cloud (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 33 days.

(21) Appl. No.: 10/658,535
(22) Filed: Sep. 10, 2003
(65) Prior Publication Data

US 2005/0030019 A1 Feb. 10, 2005

(30) Foreign Application Priority Data

Sep. 11, 2002  (FR) ............................................. 02 11282

(51) Int. Cl.$^7$ ................................................. G01V 3/00
(52) U.S. Cl. ..................................... 324/303; 324/300
(58) Field of Search ............................... 324/303, 300; 702/13, 6

(56) References Cited

U.S. PATENT DOCUMENTS

| | | | | | |
|---|---|---|---|---|---|
| 4,211,106 | A | * | 7/1980 | Swanson | 73/38 |
| 4,525,544 | A | * | 6/1985 | Nelson et al. | 525/531 |
| 4,648,261 | A | * | 3/1987 | Thompson et al. | 73/38 |
| 4,752,882 | A | * | 6/1988 | Givens | 702/13 |
| 4,926,113 | A | * | 5/1990 | Gunnink et al. | 324/694 |
| 6,484,102 | B1 | * | 11/2002 | Holmes | 702/6 |
| 6,825,658 | B2 | * | 11/2004 | Coates et al. | 324/303 |

FOREIGN PATENT DOCUMENTS

EP        0 974 839 A1    1/2000  .......... G01N/33/24

OTHER PUBLICATIONS

Sen, Pabitra N., "Resistivity of Partially Saturated Carbonate Rocks with Microporosity", Geophysics, Mar.–Apr. 1997, Soc. Exploration Geophysicists, USA, vol. 62, No. 2, pp. 415–425, XP002245236.

Ohen, Henry A., et al., "NMR Relaxivity Grouping or NMR Facies Identification is Key to Effective Integration of Core Nuclear Magnetic Resonance Data with Wireline Log", SCA Proceedings, Paper 9942, 1999, SP002245237.

Mirotchnik, Konstantin, et al., "Determination of Mud Invasion Characteristics of Sandstone Reservoirs Using a Ocmbination of Advanced Core Analysis Techniques"; SCA Proceedings, Paper 9815, 1998, XP002245238.

(Continued)

*Primary Examiner*—Brij B. Shrivastav
(74) *Attorney, Agent, or Firm*—Antonelli, Terry, Stout & Kraus, LLP

(57) ABSTRACT

A method for determining the variations of the resistivity index (RI) of a family of rock samples of complex pore structure with at least two pore networks, as a function of the water saturation (Sw), and in the presence of a non-oil conducting fluid. The volume fraction ($f_1, f_2, f_3$) occupied by each pore network and the distribution of the pore throats in the various pore networks are determined for each sample of the family. The values of coefficients relating the variation of its electrical resistivity as a function of its water saturation (Sw) are experimentally determined on a sample of the family used as a reference sample. The resistivity index (RI) of all the samples of the family is then determined on the basis of the variation of parameters describing the layout of the pore network, and using the values of the coefficients measured on the reference sample. The method allows measurement of a continuous resistivity index curve which is not obtained, as in conventional techniques, from only a limited number of points at capillary equilibrium.

3 Claims, 4 Drawing Sheets

OTHER PUBLICATIONS

Swanson, B.F., "Microporosity in Reservoir Rocks: Its Measurement and Influence on Electrical Resistivity", Log Anal. Nov.–Dec. 1985, vol. 26, No. 6, Nov. 1985, pp. 42–52.

Fleury, M., "Characterization of Porous Structures by RMN Relaxometry", Revue de L'Institut Francais de Petrole), Editions Technip, Paris, FR, vol. 53, No. 4, Jul. 1998, pp. 489–493, XP000831361.

* cited by examiner

METHOD FOR DETERMINING THE RESISTIVITY INDEX, AS A FUNCTION OF THE WATER SATURATION, OF CERTAIN ROCKS OF COMPLEX POROSITY

BACKGROUND OF THE INVENTION

1. Field of the Invention

The present invention relates to a method for determining the resistivity index RI, as a function of the water saturation, of certain rocks of complex porosity.

2. Description of the Prior Art

Evaluation of carbonate reservoirs is a particularly difficult task for petrophysicists, who still lack precise knowledge concerning the carrying properties within these porous media. In relation to siliclastic rocks, carbonates may be simpler on the mineralogical plane, but they are incomparably more complex in terms of pore structure and surface properties. The largely biological origin of the sediments, combined with various diagenetic processes, leads to complex pore structures that may be very different from one reservoir to the next. For many carbonate systems, resistivity data calibrations carried out in the laboratory contradict the observations made in the field (anhydrous production, capillary pressure) and the direct water saturation measurements performed on preserved cores.

The prior art is notably defined by the following publications:

- Bouvier L. et al., Reconciliation of Log and Laboratory Derived Irreducible Water Saturation in a Double Porosity Reservoir, Advances in Core Evaluation, edited by Worthington and Longeron, Gordon and Breach Science Publishers,
- Dixon J. R. et al. (1990), The Effect of Bimodal Pore Size Distribution on Electrical Properties of some Middle Eastern Limestone, Soc. Petr. Eng. 20601, $7^{th}$ SPE Middle Eastern Oil Show, Bahrain, pp.743–750,
- Fleury M. (1998), "FRIM: a Fast Resistivity Index Measurement Method", Proceedings of the International Symposium of the Society of the Core Analysts, Den Hague,
- Fleury M. et al. (2000) "Frequency Effect on Resistivity Index Curves Using a New Method", Proceedings of the $41^{st}$ Annual SPWLA Symposium, Dallas,
- Moore C. H. (2001) "Carbonate Reservoirs, Porosity Evaluation and Diagenesis in a Sequence Stratigraphic Framework", Developments in Sedimentology 55, Elsevier Editions,
- Petricola M. J. C. et al. (1995) "Effect of Microporosity in Carbonates: Introduction of a Versatile Saturation Equation", Soc. Petr. Eng. 29841, SPE Middle Eastern Oil Show, Bahrain, pp.607–615,
- Sen P. N. et al. (1997) "Resistivity of Partially Saturated Rocks with Microporosity", Geophysics, Vol.62, No.2, pp415–425.

Understanding and prediction of the effect of the structure of the pore network, of the wettability and of the electrical properties of carbone rocks is a real scientific challenge, theoretically as well as experimentally. In fact, correct evaluation of these parameters has a major impact on estimation of the oil in place, notably for Middle Eastern giant fields, because the difference in relation to the standard values of Archie's exponents m and n in relation to value 2 is so great that estimation of the water saturation can vary by more than 20%.

Various experimental observations have shown the existence of distinct pore populations: micropores, macropores and mesopores, with different coexistence degrees. In general, the resistivity index curve $RI(Sw)=Rt(Sw)/Ro$, where Rt is the resistivity of the rock to a water saturation Sw, and Ro the resistivity for Sw=1, cannot be described by a power law (second Archie's law $RI=Sw^{-n}$), that is n is a function of the saturation itself. Microporosity can act as a parallel path for the current, which leads to a decrease in the values of n and, therefore, to a gradual insensitivity of the resistivity to saturation, as observed on clayey sands. Microporosity can also be the cause of the low measured values of n (typically 1.45). It has also been observed that n can increase considerably under certain conditions, and there might be a connection between curve RI(Sw) and the capillary pressure curve. The increase in the values of n is also a known effect of the wettability, which tends to favor aqueous phase discontinuity and therefore to increase the resistivity to water wettability. The effect of the wettability can lead to either a sudden increase of n, or to a high value n without discontinuity, which can lead to confusion.

The experimental curves RI(Sw) which have been drawn from various prior works, already mentioned above, and from observations can have (FIG. 1) four distinct shapes which do not always meet Archie's laws:

- type I: can be typical of carbonates from the Thamama formation,
- type II: straightens at intermediate saturation and flattens at low saturation (present study),
- type III: single slope at low saturation, extrapolation at Sw=1 above Ir=1, and
- type IV: typical of oil-wet systems, high values of n that can increase further at low saturation. This is also valid for clasts.

It can thus be seen that, in the presence of rocks of complex porosity which do not meet Archie's laws, a large number of costly measurements is necessary to take account of the variability of the pore structure.

SUMMARY OF THE INVENTION

The method according to the invention determines the variations of the resistivity index (RI) of a family of rock samples of complex pore structure as a function of the water saturation (Sw), in the presence of a non-conducting fluid. The method of the invention comprises the following stages:

- for each sample of the family comprising at least a first and a second pore network, determining a volume fraction occupied by each pore network by applying to the various samples an NMR type relaxometry technique;
- for each sample of the family, measuring by mercury injection the pore throat distribution in the various pore networks;
- determining experimentally on a sample at least of the family used as the reference the values of coefficients relating the variaton of the sample's electrical resistivity as a function of the sample's water saturation; and
- determining the resistivity index (RI) of all the samples of the family on the basis of the variation of parameters describing the layout of the pore network and using the values of the coefficients measured on the reference sample.

According to a first implementation mode suited for samples comprising two pore networks, the values of the coefficients relating a total conductivity of the sample to a conductivity of the first and second pore networks and to respective water saturations of the two networks are determined from the reference sample. The resistivity index is calculated from the respective volume fractions of the two pore networks and from the value of the mean saturation from which the network with the smaller pores is invaded by the non-conducting fluid.

According to a second implementation mode suited for samples comprising a third pore network, the values of coefficients relating a total conductivity of a sample to the conductivity of the first and second pore networks and to the respective water saturations of the first two networks are determined from the reference sample. The resistivity index is calculated from the respective volume fractions of the three pore networks, from a value of a mean saturation from which the network having the smaller pores among the first two pore networks is invaded by the non-conducting fluid, and from the value of the mean saturation from which the network having the larger pores among the first two pore networks is invaded by the non-conducting fluid.

The resistivity index variations obtained by applying the method are in best agreement with the experimental curves whose examples are illustrated in FIG. 1. The method is based on a powerful experimental technique allowing measurement of a continuous resistivity index curve, unlike the conventional technique which describes curve RI only by a limited number of points at capillary equilibrium.

BRIEF DESCRIPTION OF THE DRAWINGS

Other features and advantages of the method and of the device according to the invention will be clear from reading the description hereafter, with reference to the accompanying drawings wherein.

DETAILED DESCRIPTION OF THE PREFERRED EMBODIMENTS

Figure 1:
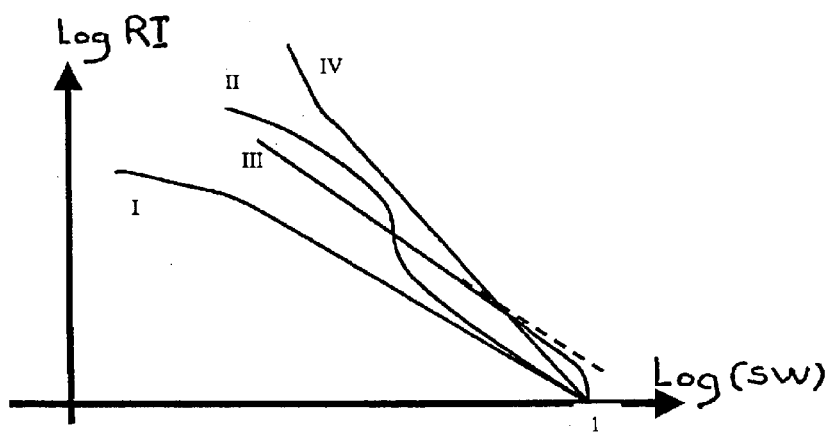
FIG. 1 shows a diagrammatic representation, in logarithmic coordinates, of various types of curves RI as a function of the water saturation Sw observed experimentally with curves I to III being due to pore structure and curve IV is typical of the effects of wettability which is not specific to carbonates.

A number of samples of the same family exist for which calculation of the resistivity index of each sample is desired. The method described hereafter allows these indices to be obtained, notably from:

experimental measurements performed on each sample of the family, giving the number of pore networks of different size and the volume fraction occupied by each pore network, as well as the pore throat distribution for each one, and an experimental measurement performed on a single sample of the family, used as a reference sample, of the variation of its electrical resistivity as a function of its water saturation (Sw).

Nomenclature

Cto=total conductivity at Sw=1

Ci=conductivity of the i-th population at $Sw_1$=1

$f_i$=NMR volume fraction of pores of the i-th population, i=1,2,3

RI=resistivity index, Rt/RoSw=mean water saturation $Sw_i$=water saturation of the i-th pore population Sc=mean saturation at which the micropores are invaded Sm=mean saturation at which the macropores are invaded $\alpha_{1,2}$=conductivity ratio $C_1/C_2$ and $C_1/C_3$ respectively.

Experimental Data on Samples

NMR Relaxation Time Measurements

The various pore networks within the rock samples and the volume fraction occupied by each network are first determined by means of a well-known NMR type relaxometry method. An example of such an NMR relaxometry method is for example described in French patent application EN-02/ . . . filed by the applicant.

We present the measurements performed on three selected carbonate samples. By applying an NMR type known relaxometry method, it is seen that all the samples are characterized by a double or triple pore size distribution. The first one is a reservoir carbonate sample from the Middle-East, classified as a packstone. It was cleaned by means of different solvents at high temperature before being subjected to the measurements. Under ambient conditions, the experiment was carried out with refined oil and synthetic reservoir brine. The experiment carried out under reservoir conditions was conducted with filtered degassed reservoir oil at the reservoir pressure. After cleaning, the wettability of the sample is characterized by a moderate water wettability and, after aging, by a high oil wettability. The other two samples are outcrop carbonates (water-wet). The porosity of the Brauvillier limestone (BL) is essentially intergranular and due to the oolite cortex. The porosity of the Estaillade limestone is both inter and intragranular. The pore populations are separated by a factor 10 at least.

Resistivity Index Measurements

The resistivity index of the samples is then measured. The fast resistivity index measurement method (FRIM) described in patent EP-974,839 filed by the assignee can be advantageously used.

According to this method, a forced oil-water displacement is carried out on a small core of length 2.5 cm and diameter 4 cm for example. This displacement is very close to a porous plate displacement method, except that capillary equilibrium is not necessary. Under ambient conditions, only two or three pressure stages are used. Under reservoir conditions, when dead or crude oil is used, each pressure stage is prolonged for the time required to obtain wettability stabilization at a given saturation. Drainage is thus carried out in approximately two to three weeks, which typically corresponds to the kinetics of the chemical processes linked with aging. The simplicity of this method lies in the fact that it just requires real-time recording and plotting of the mean saturation and resistance to obtain a continuous resistivity index curve free of any artefact. The key point is due to the fact that the radial geometry of the electrodes allows examining the whole volume of the sample and to compensate for the non-uniform saturation profile which appears in the absence of capillary equilibrium.

Under ambient conditions, the radial-electrode cell described for example in the aforementioned patent EP-A-974,839 is used. The complex impedance measurements were carried out at a fixed frequency of 1 kHz and the real part was extracted to calculate the resistivity index. The highest capillary pressure applied was 12 bars (for an interfacial tension y=35 mN/m; under reservoir conditions, with crude oil, the maximum capillary pressure was reduced proportionally to the interfacial tension).

Conductivity Models

Double-Porosity Conductivity Model (DPC)

The goal is to explain the bending of curves RI at low saturation (type I, FIG. 1). The double-porosity model considered here is basically very close to those proposed for clayey sands, where the clays present at the surface of the pores constitute a parallel path for the current. For carbonates, we assume the existence of two pore networks having parallel electrical conductivities is assumed. The two main ingredients in the model are the description of the pore network invasion during drainage and the description of the electrical layout of the two different pore populations.

The first network 1 (macropores for example) represents the major part of the pore volume, whereas the second network 2 (micropores) only represents a small fraction thereof, which is not necessarily greater than the percolation thresholds. The saturation of each network, $Sw_1$ and $Sw_2$, which are related to the measured mean saturation Sw is first considered by:

$$Sw = f_1 Sw_1 + f_2 Sw_2 \text{ where } f_1 + f_2 = 1 \qquad (1).$$

The quantities $f_1$ and $f_2$ represent the pore volume fraction of each population. These fractions were evaluated by means of the NMR relaxometry technique. We then assume that the networks are invaded by oil at different capillary pressures; the oil reaches the small pores at a higher pressure than the pressure observed for the larger pores. From the capillary pressure curve previously drawn, this pressure corresponds to a mean saturation Sc which can be deduced from the curves obtained by mercury injection (showing the pore throat distribution). $Sw_1$ can be expressed as a function of Sw at high saturation Sw:

$$Sw_1 = \frac{Sw + f_1 - 1}{f_1}, \quad Sw_2 = 1 \text{ for } Sw \geq Sc \qquad (2)$$

Below Sc, relations $Sw_1=f(Sw)$ and $Sw_2=f(Sw)$ require other hypotheses. The assumption (i) is a linear relation and (ii) that $Sw_1 \to 0$, $Sw_2 \to 0$ when $Sw \to 0$.

It is deduced that:

$$Sw_1 = \frac{f_1 + Sc - 1}{f_1 Sc} Sw,$$

$$Sw_2 = \frac{Sw}{Sc} \text{ for } Sw \leq Sc \qquad (3)$$

The conductivity of each network is now considered. In case of an initial brine saturation, the total conductivity $Ct_0$ for the two networks in parallel will be:

$$Ct_0 C_1 + C_2 = C_1(1+\alpha) \text{ where } C_2 = \alpha C_1 \qquad (4).$$

Parameter $\alpha$ is the conductivity ratio of the two 100% saturated networks. From Archie's first law, $C_1$ and $C_2$ are assumed to be related to the pore volume fraction of each population and, therefore, that a is of the order of ratio $f_2/f_1$. When the two networks are invaded by oil, each conductivity is assumed to be related to the saturation by a power law (as in Archie's second law). The total conductivity in the two saturation ranges is as follows:

$$Ct = Sw_1^{n1} C_1 + C_2 \text{ for } Sw \geq Sc \qquad (5)$$

$$Ct = Sw_1^{n1} C_1 + Sw_2^{n2} C_2 \text{ for } Sw \leq Sc \qquad (6).$$

By means of equations 4, 5 and 6, the resistivity index RI is as follows:

$$RI = \frac{Ct_0}{Ct} = Sw_1^{-n1} \frac{1+\alpha}{1+\alpha Sw_1^{-n1}} \text{ for } Sw \geq Sc \qquad (7)$$

$$RI = Sw_1^{-n1} \frac{1+\alpha}{1+\alpha Sw_1^{-n1}/Sw_2^{-n2}} \text{ for } Sw \leq Sc \qquad (8)$$

When a pore population is in the dominant position (network 1 in the present case), functions RI are governed by the resistivity properties ($n_1$) of this population. Equations 7 and 8 are essentially similar to the formulas used for clayey sands, except that a second exponent $n_2$ is introduced which characterizes the second network.

Figure 3A:
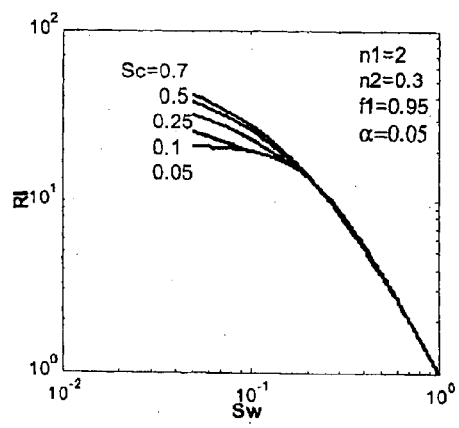
FIGS. 3a and 3b show the sensitivity of the model with two pore networks (DPC) to the saturation Sc at which the micropores are invaded by oil (3a) and to α which is the initial conductivity ratio of the two pore populations (3b)
Figure 3B:
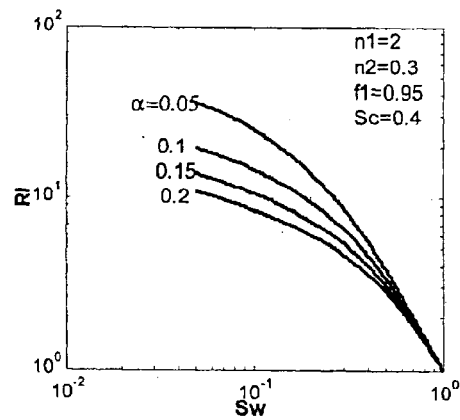
Figure 4A:
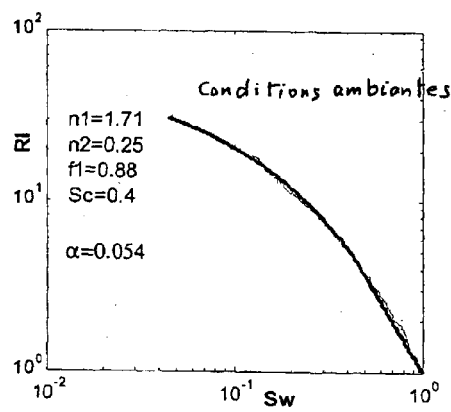
FIGS. 4a and 4b show the application of model DPC to sample RC at ambient temperature (4a) and under the reservoir conditions with dead oil (4b) with the experimental curve being drawn as a thin line and the model being drawn as a thick line with parameters $n_1$, $n_2$ and α being adjusted, $f_1$ and Sc being measured.
Figure 4B:
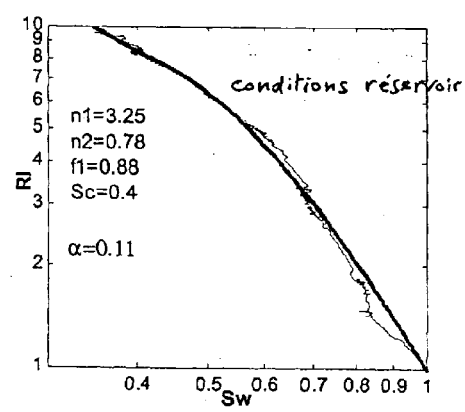

In the DPC model, there are in total 4 parameters $n_1$, $n_2$, $\alpha$ and Sc. For a given experimental curve, Sc is measured separately during a mercury injection experiment, whereas the other parameters are adjusted. A variation range is however observed for a around $f_2/f_1$, for which a physical explanation exists. At high saturation Sw, the slope on the log—log scale of RI(Sw) is $-n_1$ and, at low saturation, the slope is $-n_2$. To a certain extent, Sc and $\alpha$ compensate for one another (FIG. 3), but a is the most sensitive parameter which controls the final value of RI. It can be noted that the case Sc=0.05 presented in FIG. 3 corresponds to a situation where the second network is not invaded by oil, which gives a horizontal asymptote.

Figure 2:
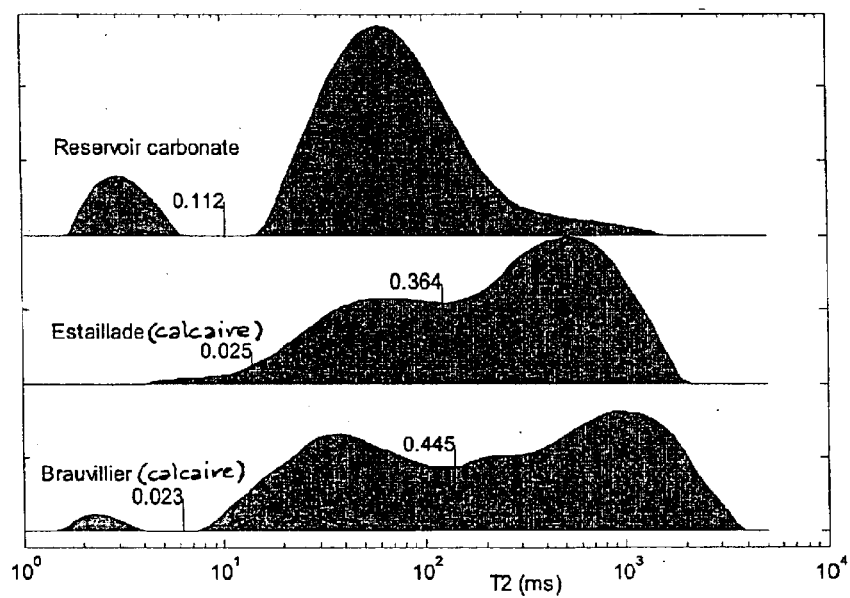
FIG. 2 shows a pore size distribution of three carbonates studied: (reservoir carbonate, Estaillade limestone and Brauvillier limestone) obtained by NMR with the pore volume fraction being to the left of the vertical segment.

The parameters of the model were adjusted in order to correspond to the experimental curve RI measured on sample RC. The value of Sc=0.4 was deduced from the elbow of the capillary pressure curve obtained by mercury injection and the volume fraction $f_1$=0.88 macropores (network 1) was deduced by NMR (FIG. 2). Despite the low permeability of the sample, the lowest saturation obtained is very low (4%), which allows good determination of the parameters of the model under ambient conditions. The initial slope of curve RI is $n_1=1.71$; it characterizes network 1. Network 2 is very weakly sensitive to saturation ($n_2=0.25$) and does not behave like a standard network. However, the initial conductivity ratio $\alpha=0.054$ of network 1 to 2 is of the order of $f_2/f_1=0.136$. Under reservoir conditions (oil wettability conditions), a high increase of $n_1$ is observed, but curve RI is still not linear on the log—log scale. Characteristics $n_2=0.78$ and $\alpha=0.11$ of the second network are also slightly modified, but the precision concerning these parameters is lower that under ambient conditions because the saturation reached (at the same capillary pressure) is much higher and close to Sc.

Approximate Formula in the Case of the DPC Model

An approximate formula reducing relations 7 and 8 to a single formula, which is valid for the type I curves is as follows. Note that:

$$Sw_2{}^{n2}Sw_1{}^{-1} \approx Sc^{-n2}Sw^{n2-n1} \approx Sw^{n2-n1} \text{ with } Sw_1 \approx Sw \text{ and } Sc^{-n2} \approx 1 \quad (15)$$

which gives $f_2 \ll f_1$. Since $n_2 \ll n_1$, equations 7 and 8 can be approximated by:

$$RI = Sw^{-n1} \frac{1+C}{1+CSw^{n2-n1}}. \quad (16)$$

Using the 3 parameters $n_1$, $n_2$ and C is sufficient to describe the data with precision by means of equation 16. Here, the meaning of C is approximately the same as a and it can depend on the temperature. The formulation given in equation 16 can be used to describe standard experiments carried out at capillary equilibrium where only a limited number of points is available.

Triple-Porosity Conductivity Model (TPC)

The goal is to explain the straightening of curves RI at intermediate or high saturation, and their bending at low saturation on the log—log scale (types II and III, FIG. 1). Complex carbonates can have three pore populations referred to, for simplification reasons, as micro, macro and mesopores (3, 2 and 1 respectively). As in the double-porosity model, the saturation of the 3 populations is considered:

$$Sw=f_1Sw_1+f_2Sw_2+f_3Sw_3 \text{ where } f_1+f_2+f_3=1 \quad (9)$$

Here again, the invasion of these populations by oil during drainage is assumed to be sequential. If network 1 is invaded first, a mean saturation Sm is defined at which network 2 is invaded:

$$Sw_1 = \frac{Sw - f_2 - f_3}{f_1}, Sw_2 = 1 \; Sw_3 = 1 \text{ for } Sw \geq Sm \quad (10)$$

Below Sm, it is possible to imagine many scenarios. In general, linear relations for functions $Sw_1(Sw)$ and $Sw_2(Sw)$ are assumed. According to a possible scenario, $Sw_1 \rightarrow 0$ and $Sw_2 \rightarrow 0$ when $Sw \rightarrow Sc$ is assumed. Sc is the saturation at which the micropores are invaded. It follows therefrom that:

$$Sw_1 = \frac{Sw - f_2 Sw_2 - f_3}{f_1}, \quad (11)$$

$$Sw_2 = \frac{Sw - Sc}{Sm - Sc},$$

$$Sw_3 = 1 \text{ for } Sc \leq Sw \leq Sm$$

Figure 5:
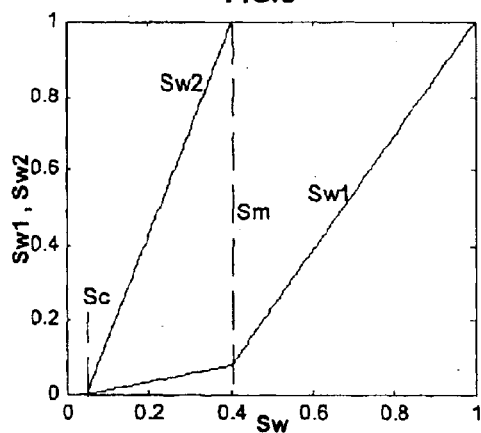
FIG. 5 shows an invasion scenario in the model with three pore networks (TPC)

This invasion scenario is summarized in FIG. 5. Typically, a situation is considered where $f_3 \ll f_1$ and $f_1 \approx f_2$, and the micropores (network 3) are invaded at a pressure that is much too high to be observed during the experiment.

Figure 6:
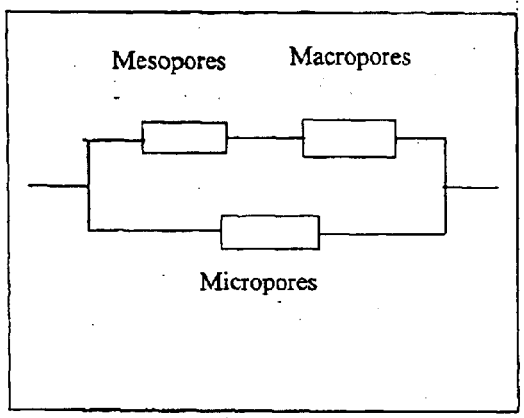
FIG. 6 shows an electrical layout modelling of the three networks in the TPC model.

Consider now the conductivity of these populations. Networks 1 and 2 are assumed in series, whereas network 3 is in parallel as shown in FIG. 6. The arrangement in series may seem to contradict a sequential invasion by oil (which is an essentially parallel mechanism), but such a situation is possible. At Sw=1, conductivity $Ct_0$ of the system shown in FIG. 6 is as follows:

$$Ct_0=(C_1{}^{-1}+C_2{}^{-1})^{-1}+C_3=C_1[(1+\alpha_1{}^{-1})^{-1}+\alpha_2] \text{ where } C_2=\alpha_1 C_1, C_3=\alpha_2 C_1, \quad (12).$$

In the two saturations ranges, it is obtained that:

$$Ct=C_1[(Sw_1{}^{-n1}+\alpha_1{}^{-1})^{-1}+\alpha_2] \text{ for } Sw \geq Sm \quad (13)$$

$$Ct=C_1[Sw_1{}^{-n1}+Sw_2{}^{-n2}\alpha_1{}^{-1})^{-1}+\alpha_2] \text{ for } Sc \leq Sw \leq Sm \quad (14).$$

The resistivity index can be calculated from equations 12 to 14. For the measured values of $f_1$, $f_2$ and $f_3$, $n_1$, $n_2$, $\alpha_1$, and $\alpha_2$ have to be adjusted to the experimental data. As in the DPC model, $\alpha_1$ is expected to be of the order of $f_2/f_1$ and $\alpha_2$ of the order of $f_3/f_1$.

Figure 7:
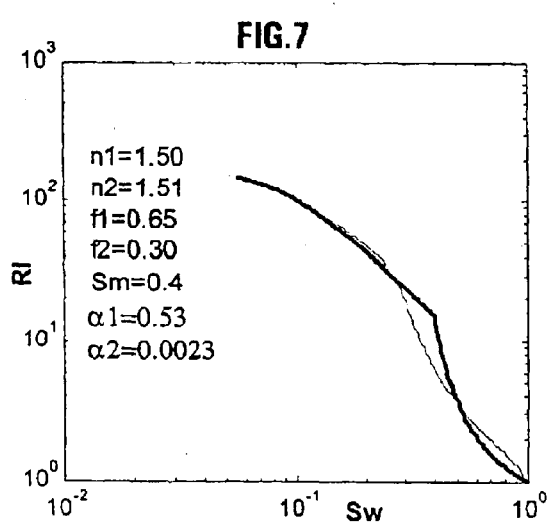
FIG. 7 shows a measured (thin line) and model (thick line) curve RI for sample EL (Estaillade limestone)
Figure 8:
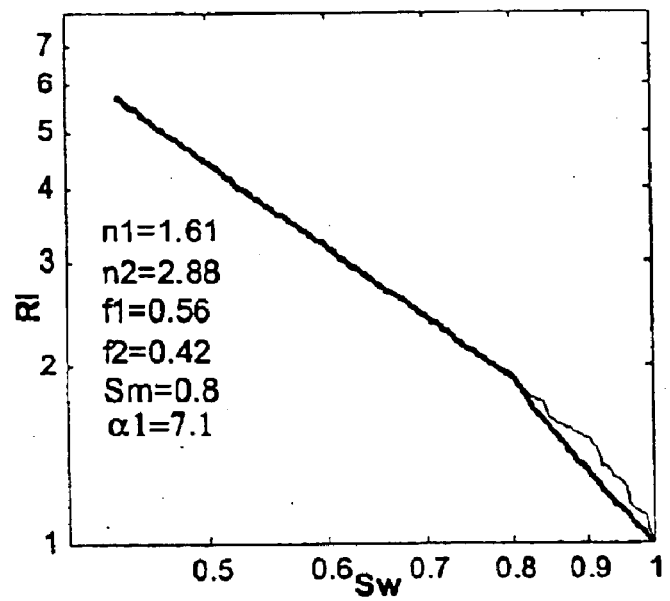
FIG. 8 shows a measured (thin line) and model (thick line) curve RI for sample BL (Brauvillier limestone)
Figure 9:
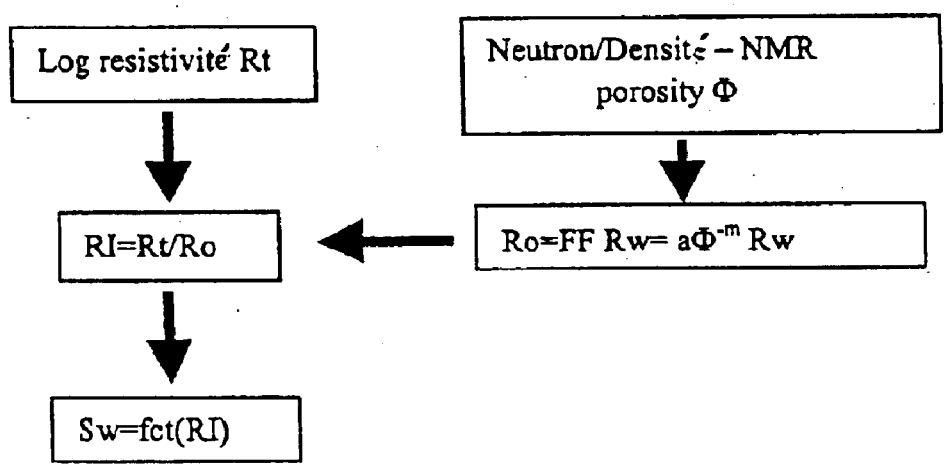
FIG. 9 shows a simplified calibration sequence for the resistivity logs with for non-Archie type rocks, Sw(RI) is necessary and the laboratory data generally providing relation RI(Sw).

This model was tested with resistivity index curves measured on samples EL and BL. On sample EL (FIG. 7), straightening of the curve at high saturation is reproduced qualitatively at high saturation and flattening at low saturation is reproduced. A discontinuity at Sm (deduced from the elbow of the capillary pressure curve obtained by mercury injection) is observed because of a sudden modification of relation $Sw_1(Sw)$ (as shown in FIG. 5). After adjustment, the two dominant pore populations have similar characteristics ($n_1=n_2=1.5$). The third population, which behaves like a parallel circuit, is not invaded by oil and it is only characterized by conductivity ratio $\alpha_2$. On sample BL (FIG. 8), curve RI can be explained by a similar mechanism of resistance in series, but with a very high value Sm. The two networks observed have very different values n and that network 2 is much less conducting than network 1 ($\alpha_1=7.1$).

The method according to the invention finds applications notably in the sphere of hydrocarbon reservoir development.

What is claimed is:

1. A method for determining variations of resistivity index of a family of rock samples as a function of water saturation, in the presence of a non-electrically conducting fluid, comprising:

for each sample of the family of rock samples comprising at least first and second pore networks, determining a volume fraction occupied by each pore network by applying to the rock samples an NMR type relaxometry technique;

for each sample of the family of rock samples, measuring by mercury injection a pore throat distribution in the at least first and second pore networks;

determining experimentally on a sample used as a reference from at least the family of rock samples values of coefficients relating variation of electrical resistivity of the sample used as the reference as a function of water saturation of the sample used as the reference; and determining the resistivity index of all the samples of the family of rock samples on a basis of a variation of parameters describing a layout of the pore networks and using values of the coefficients measured from the sample used as the reference.

2. A method as claimed in claim 1, wherein values of the coefficients relating a total conductivity of the sample used as a reference to conductivity of the first and second pore networks and water saturation of the first and second networks are determined from the sample used as a reference with the resistivity index being calculated from the volume fractions of the first and second pore networks and from a value of a mean saturation from which one of the first and second networks with smaller pores is invaded by the non-electrically conducting fluid.

3. A method as claimed in claim 1, wherein for a sample from a third pore network, values of the coefficients relating total conductivity of the sample from the third pore network to conductivity of the first and second pore networks and water saturations of the first and second networks are determined from the sample used as the reference, with the resistivity index being calculated from respective volume fractions of the first, second and third pore networks, from a value of mean saturation from which the network having smaller pores among the first and second pore networks is invaded by the non-electrically conducting fluid, and from a value from which the network having larger pores among the first and second pore networks is invaded by the non-electrically conducting fluid.

\* \* \* \* \*